(12) United States Patent
Satragno et al.

(10) Patent No.: US 7,676,256 B2
(45) Date of Patent: Mar. 9, 2010

(54) IMAGING APPARATUS

(75) Inventors: Luigi Satragno, Genoa (IT); Eugenio Biglieri, Masio (IT)

(73) Assignee: Esaote S.p.A., Casale Monferrato (IT)

( * ) Notice: Subject to any disclaimer, the term of this patent is extended or adjusted under 35 U.S.C. 154(b) by 1307 days.

(21) Appl. No.: 10/216,887

(22) Filed: Aug. 13, 2002

(65) Prior Publication Data

US 2003/0083572 A1     May 1, 2003

(30) Foreign Application Priority Data

Aug. 14, 2001   (IT) .................... SV2001A0029

(51) Int. Cl.
*A41B 5/05*        (2006.01)
(52) U.S. Cl. .............. 600/417; 600/421; 600/424; 600/429
(58) Field of Classification Search ............ 600/407, 600/411, 423, 424, 417, 427, 462, 130, 421, 600/429
See application file for complete search history.

(56) References Cited

U.S. PATENT DOCUMENTS

| | | | |
|---|---|---|---|
| 5,143,068 A * | 9/1992 | Muennemann et al. ...... 600/422 |
| 5,176,646 A * | 1/1993 | Kuroda ...................... 604/154 |
| 5,240,011 A | 8/1993 | Assa | |
| 5,485,839 A * | 1/1996 | Aida et al. .................. 600/427 |
| 5,534,778 A * | 7/1996 | Loos et al. .................. 324/318 |
| 5,575,287 A * | 11/1996 | Eydelman .................... 600/422 |
| 5,706,812 A | 1/1998 | Strenk et al. | |
| 5,817,106 A | 10/1998 | Real | |
| 5,957,934 A | 9/1999 | Rapoport | |
| 6,019,724 A * | 2/2000 | Gronningsaeter et al. ... 600/439 |
| 6,060,883 A * | 5/2000 | Knuttel ...................... 324/318 |
| 6,079,681 A * | 6/2000 | Stern et al. ................ 248/278.1 |
| 6,529,764 B1 * | 3/2003 | Kato et al. .................. 600/411 |
| 6,546,279 B1 * | 4/2003 | Bova et al. .................. 600/429 |
| 6,665,554 B1 * | 12/2003 | Charles et al. ............. 600/427 |
| 6,726,650 B2 * | 4/2004 | Schneider et al. ............. 604/82 |

FOREIGN PATENT DOCUMENTS

| | | |
|---|---|---|
| EP | 1 090 594 A | 4/2001 |
| JP | 09-924233 | 4/1997 |
| WO | 01/01845 | 1/2001 |

OTHER PUBLICATIONS

C.K. Kuhl, "MR-Guided Lesion Localization and Biopsy of the Breast"; Interventional Magnetic Resonance Imaging, Springer-Verlag, 1998, pp. 137-146, XP-002199034.

* cited by examiner

*Primary Examiner*—Long V Le
*Assistant Examiner*—Ellsworth Weatherby
(74) *Attorney, Agent, or Firm*—Buchanan Ingersoll & Rooney PC

(57) ABSTRACT

A combined imaging apparatus having a magnetic resonance imaging apparatus with at least one transmitting coil for exciting the matter of a body under examination or of a part thereof and at least one coil for receiving the signals transmitted by the body under examination or a part thereof, as well as an electronic unit for processing the received signals to create a diagnostic image and including a device for supporting and/or guiding at least one diagnostic and/or therapeutic tool. The combined apparatus further including an echographic imaging apparatus.

47 Claims, 7 Drawing Sheets

IMAGING APPARATUS

BACKGROUND OF THE INVENTION

1. Field of the Invention

The invention relates to a imaging apparatus comprising a magnetic resonance imaging (MRI) apparatus, with at least one transmitting coil for exciting the matter of a body under examination or of a part thereof and at least one coil for receiving the signals transmitted by the body under examination or a part thereof, as well as electronic means for processing said received signals to create an image and which apparatus has further means for supporting an guiding a surgical or therapeutic tool.

2. Description of Related Art

As is known, MRI examinations are often combined with the use of various tools, which may consist of diagnostic assistance instruments or of therapeutic instruments. This may be the case, for instance, of shoulder dedicated MRI apparatuses, wherein contrast agents are often to be injected in the region under examination. The perfusion of said contrast agents shall be as accurate as possible and requires a critical time selection, which may not be easy, especially due to the anatomic peculiarities of the shoulder which, as is known, is a very complex anatomic region, especially when said operations are carried out in a wholly manual manner. In this case, the success of these operations only depends on the skills and expertise of the operator. Any error in the selection of the injection point and/or of the needle orientation, or a poor synchronization with MRI operations may lead to less than optimal images and require a new injection. In particular cases, this may even cause damages to tissues. Similar or even more serious difficulties may be encountered when the MRI apparatus is used in combination with other types of diagnostic and/or therapeutic tools, to be further mentioned hereafter in the description.

Document EP 1090 594 and U.S. Pat. No. 5,706,812 discloses an MRI apparatus having an RF receiving coil comprising means for supporting a therapeutic tool such as a syringe or a needle.

The supporting means helps in correctly aiming the tool against the zone to be treated while the imaging apparatus helps in viewing the tool and the part where the tool acts for better controlling the position, the orientation and the effect of the tool.

Although the known devices according to the above mentioned documents work, there are some tools and some tissue which depending on the kind of material or tissue and the form or shape of the tool or the structure of the tissue are not well imaged by the MRI apparatus.

OBJECTS AND SUMMARY

Therefore, this invention has an object of improving the imaging capability of the imaging apparatus for better viewing the part of the body to be treated and the tool which is used, by collecting more or better information thus improving the performances of the imaging apparatus and the precision of positioning and orienting the tool. Particularly, there is a need to define in a reliable manner the position and the orientation of the diagnostic and/or therapeutic instrument, whose use is provided in combination with MRI, in relation to the particular anatomy of the region under examination and to the anatomy of the individual patient, and to obtain an optimized synchronization between the various diagnostic and/or therapeutic times, or anyway a better synchronization than is currently possible.

The invention achieves the above purposes by providing an apparatus as described hereinbefore which includes an echographic or ultrasound imaging apparatus having a probe for transmitting and receiving pulses as well as electronic means for reconstructing an image from the pulses and means for supporting and/or guiding the ultrasound probe which are provided in combination with the means for supporting the tool.

These supporting and/or guiding means for the tool and for the ultrasound probe may be associated with the receiving coil.

This supporting and/or guiding means for the ultrasound probe and for the tool may be integrated in a unique element or may be separate and independent from each other.

The apparatus may include a receiving coil case or enclosure made of a material which does not interfere with Magnetic Resonance signals, generally plastic, whereon the probe and the tool supporting and/or guiding means are supported and/or fastened and/or associated. This arrangement allows to reduce the total size of the apparatus and provides a considerable construction simplification. This also allows an easier location of the probe and of the diagnostic and/or therapeutic instrument at least partly inside the MRI volume.

Said supporting and/or guiding means may be provided in an external or internal position relative to the enclosure of the receiving coil.

These supporting and/or guiding means may have for the probe and/or for the tool one, two but preferably at least three degrees of freedom with respect to the enclosure of the receiving coil, in such a manner as to allow to accurately aim at the region of interest.

The tool and the probe may be independent or they may be movable together at least for some of the degrees of freedom provided.

These supporting and/or guiding means may be of such a type as to allow the probe and the diagnostic and/or therapeutic tool to be displaced in their axial direction independently one form the other or together.

According to an improvement, these supporting and/or guiding means may be of such a type as to allow the probe and the tool to be displaced independently one from the other or together in one or more directions transverse to each other and to the axial direction, particularly in three perpendicular directions, i.e., oriented in space along three Cartesian axes.

In accordance with a further improvement, these supporting and/or guiding means may be of such a type as to allow the probe and the tool to be swung/tilted independently one from the other or together in at least one plane containing the axis of the tool and/or of the probe, but may be further improved in such a manner as to allow the probe and the tool to be swung/tilted independently or together in at least two non parallel, i.e., transverse planes, which contain the axis of the tool and/or of the probe.

A preferred arrangement provides that these supporting and/or guiding means are of such of type as to allow the probe and/or the tool to be tilted in all directions independently one from the other or together.

In accordance with a preferred embodiment of the invention, these supporting and/or guiding means may consist of a through hole for the probe and a through hole for the tool which holes are formed in the coil enclosure or in an external extension thereof, and designed to accommodate the probe and the tool.

This through hole may have such an internal size as to allow the probe or the tool to slide inside the body under examination in the axial and/or penetration direction.

According to a highly advantageous improvement, this housing hole may accommodate an interchangeable element allowing adaptation to the type of probe and/or of tool in use from time to time.

This adapter element may consist of a sleeve, wherein the probe and/or the tool, particularly an injection syringe, is introduced, the sleeve having such an internal size as to allow the probe and/or the tool to slide in its axial direction.

According to yet another improvement, the probe and/or the tool may have one or more slides for axial slidable engagement in corresponding guides provided on the inner surface of the probe and/or the tool housing hole or sleeve, or vice versa.

Advantageously, the probe and/or the tool housing hole or the probe and/or the tool-holding sleeve may be formed in a supporting member which is displaceable in one, two but preferably three directions transverse, particularly perpendicular to each other, i.e., oriented in space along three cartesian axes, one of which corresponding to the axial direction of the probe and/or the tool. The displacements of the probe and of the tool according to only some or all of the direction provided may be carried out independently for the probe and for the tool or the two parts execute at least some of the said displacements together.

The probe and/or the tool supporting members may be fastened on a first carriage for axial slidable engagement of the probe and/or of the tool on at least one first guide.

This first guide may be carried by a second carriage which is slidably engaged in a direction perpendicular to the probe and/or to the tool axis on at least one second guide, which in turn may be carried by a third carriage which is slidably engaged on at least one third guide, the latter being fastened to the coil enclosure, in another direction, perpendicular both to the first direction and to the probe and/or to the tool axis.

A highly advantageous improvement provides that the probe and/or the tool supporting member has means for swinging or tilting the probe and/or the tool axis relative to a predetermined direction, particularly a substantially vertical direction relative to the body or the part thereof under examination.

These tilting means may consist of a swinging suspension element, particularly a spherical element, wherein a probe or a tool housing hole is formed, which element is housed in a corresponding spherical seat provided inside the supporting member.

The probe and/or the tool may be displaced manually, or alternatively motor driven, manually controlled displacing means may be provided for one or more displacements, which means may be of the mechanical, electrical, electromechanical, pneumatic and/or hydraulic type.

These motor driven means may consist of at least one combination, for each type of displacement, of a motor driven pinion and of a corresponding rack, or of any other means being suitable for the purpose.

The diagnostic and/or therapeutic functions of the tool and/or the functions of the probe may be operated manually, or automatic, manually controlled operation means may be provided.

Automatic control means may be also provided for displacing and/or operating the probe and/or the tool.

These control means may consist of one or more software programs loaded in a control unit which, after displaying and interpreting an acquired image, controls in a predetermined manner the tilt and/or displacement of the probe and/or the tool and/or the operation of the diagnostic and/or therapeutic functions thereof.

This diagnostic and/or therapeutic tool may consist of a syringe or a needle, particularly for injecting contrast agents.

Advantageously, automatic means for pushing the syringe plunger and/or for automatically supplying the needle with an appropriate dose of a diagnostic and/or therapeutic substance drawn from an external tank through an appropriate tube.

Alternatively thereto or possibly in combination therewith, this diagnostic and/or therapeutic tool may consist of a biopsy needle, and/or a microwave and/or RF antenna and/or a cryotherapy probe and/or an infrared probe, and/or a surgical tool, particularly a curet or suction tool and/or any other diagnostic and/or therapeutic tool whose action may be required in combination with the MRI apparatus.

A particular kind of therapeutic tool may consist of an additional ultrasound (US) probe for irradiating anatomic parts with sound. As is known, a type of ultrasound may be used for a therapeutic purposes, for instance by using the potential destructive action thereof on neoplastic tissues or the like.

A preferred embodiment of the invention is provided by a so-called dedicated apparatus which, as is known, has a comprehensively small size, and in which the receiving coil also has a small size, for imaging limited anatomic parts of a body under examination, particularly shoulders.

This apparatus may be provided with a shoulder imaging coil of the closed type, particularly having an essentially annular shape, or of the open type, particularly having a C shape.

A particular advantage of the combination of an MRI imaging apparatus with an ultrasound imaging apparatus results from the following. MRI sequences may be very long, whereby advantages may be obtained from using ultrasound imaging to orient the tool, particularly an injection needle. Once the latter is in the proper position, the ultrasound probe may be disabled, the contrast agent may be injected, and the MRI excitation sequences may be initiated, followed by tissue transmitted sequences.

The ultrasound probe may be supported and/or displaced and/or operated manually, or there may be provided, wholly or partly, supporting and/or displacing and/or operating means like those described above, which may assist the operator in aiming operations even for the ultrasound probe.

The apparatus according to the invention is a so-called combined apparatus, i.e., used for Magnetic Resonance imaging and ultrasound imaging, particularly operating in a time-sharing mode, which allows to optimize the functions of electronic image processing means.

According to an advantageous improvement, the ultrasound probe may include means for detecting the position of the probe by MRI, so that the position of the individual ultrasound scan sections may be defined relative to MRI images and that the desired relations between the two image types may be established.

Moreover, the means for supporting and/or displacing the ultrasound probe and/or the probe itself may have analog or digital, mechanical, electromechanical, electronic or optoelectronic means for detecting the position of the ultrasound probe relative to the anatomic part under examination and/or to the Magnetic Resonance imaging volume.

The advantages of this invention are self-evident from the above, and consist in that a stable structure is provided for supporting a diagnostic and/or therapeutic tool, e.g. a syringe or a needle and a ultrasound probe, which may assume and maintain more easily a defined position relative to the body under examination or a part thereof (total body mode and dedicated mode). By this arrangement, the injection may be performed in a much more accurate manner and with no risk for the patient, especially when compared to manual displacement of the syringe or needle. Thanks to the inventive apparatus, both the anatomy of the region under examination and the image of the needle may be simultaneously displayed, whereby it is possible to get closer to the region of interest, and to avoid a repeated injection or even damages. The possibility of integrating mechanical instrument displacement and/or orientation mechanisms further simplifies the operator's task, whereas a wholly automatic control of the orientation and introduction of the needle may be provided, with specific injection times to improve the synchronization between contrast agent perfusion in the region under examination and imaging. It is also possible to evaluate very accurately not only the position but also the intensity of perfusion. The possibility of also integrating an ultrasound probe considerably increases the versatility of the apparatus.

BRIEF DESCRIPTION OF THE DRAWINGS

Further characteristics and advantages of the invention will appear more clearly from the following detailed description of the annexed figures, in which:

FIG. 13 is the same view as FIG. 10, motor driven means being provided for displacing and orienting the syringe or the like.

DETAILED DESCRIPTION OF PREFERRED EMBODIMENTS

Figure 1:
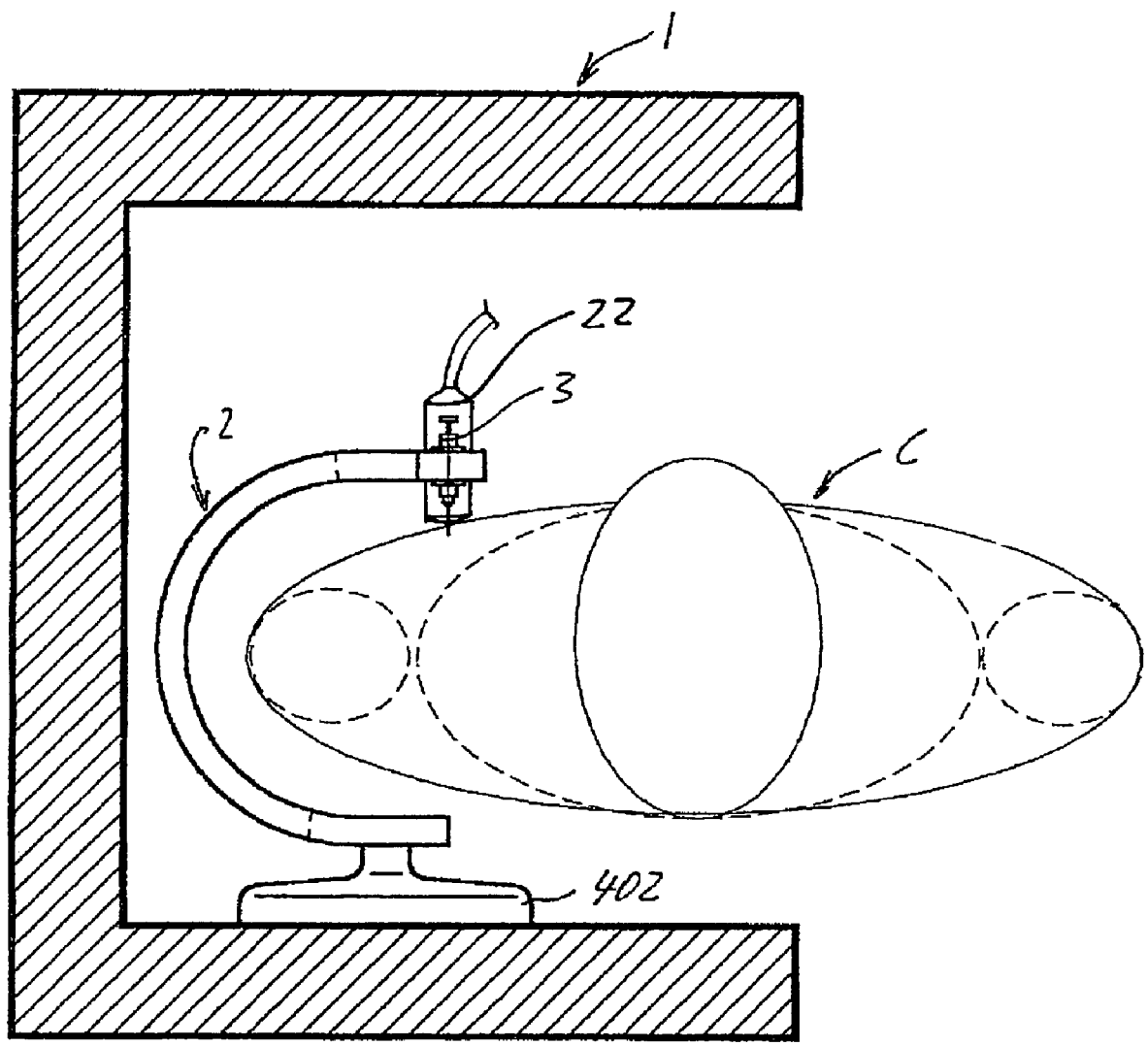
FIG. 1 shows a sectional view of an embodiment of this invention having a first type of receiving coil, with the patient in the MRI examination position.

Referring to FIG. 1, an embodiment of a dedicated combined MRI imaging and ultrasound imaging apparatus of this invention is shown. The example illustrated and described and particularly related to the examination of the shoulder is not to be considered a limitation of the present invention which may be applied to whatever anatomical district or whatever kind of body or part under examination. As is known, the above mentioned dedicated type of apparatus has the advantage of a relatively low cost and of a considerable comfort, versatility and ease of use and installation, particularly when compared with larger apparatuses. This apparatus for imaging a body C under examination or a part thereof comprises a magnetic structure 1 having at least two opposite poles which define an intermediate cavity, between which a static magnetic field is generated in a predetermined imaging volume of said cavity. The cavity may be accessed from one or more openings of the magnetic structure 1. The body under examination C, or a part thereof, is inserted in the cavity with the region to be examined passing through the imaging volume. The apparatus further includes at least one transmitting coil, having the purpose of sending a sequence of Radio Frequency nuclear spin exciting electromagnetic pulses in a predetermined order, and at least one receiving coil 2 which records the nuclear emissions relative to the transmitted electromagnetic pulses.

As is known, due to the low intensity of the MRI signals transmitted by nuclei, the receiving coil 2 must have such a size and a shape as to be as close as possible to the body C under examination. The receiving coil 2 includes an external enclosure or a covering and finishing case. This case is made of a material which does not interfere with MRI, generally plastic. The coil 2 may be further provided with a bearing and supporting pedestal 402.

Figure 2:
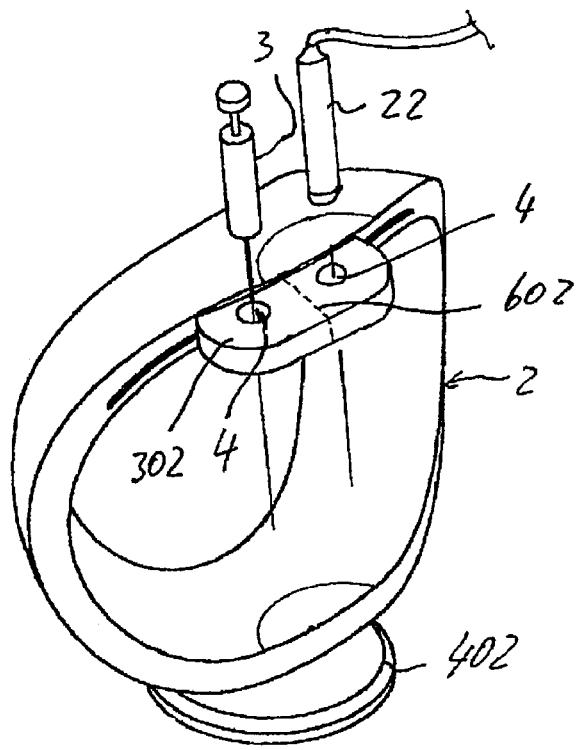
FIGS. 2 and 3 are two different perspective views of a second embodiment of a receiving coil according to the invention and being associated to a supporting member for an ultrasound probe and for a diagnostic or therapeutic tool.
Figure 3:
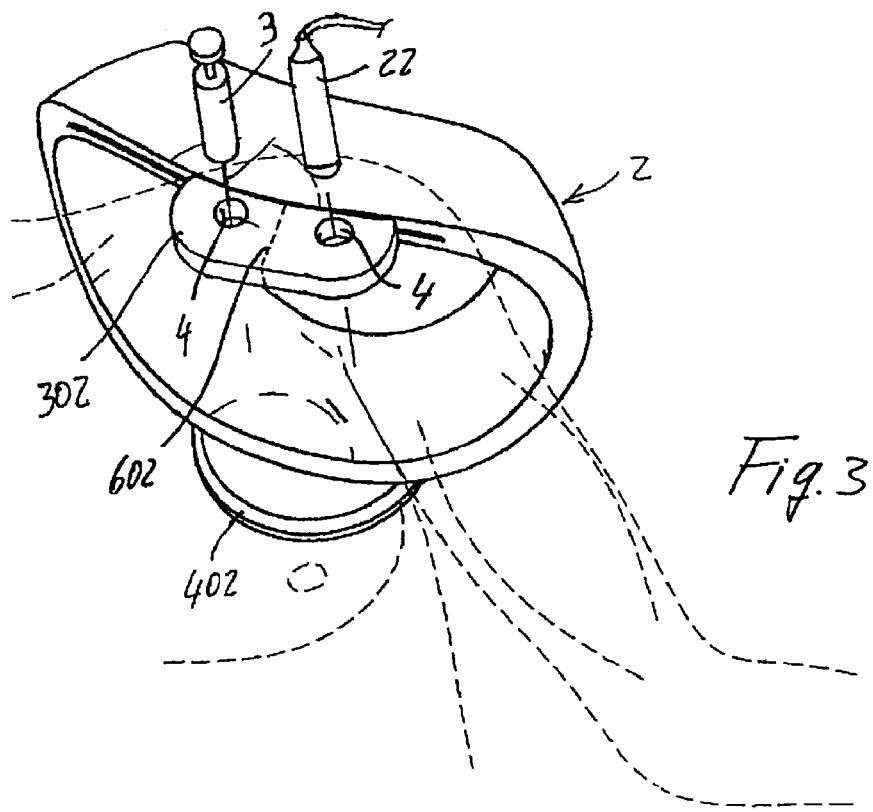
Figure 5:
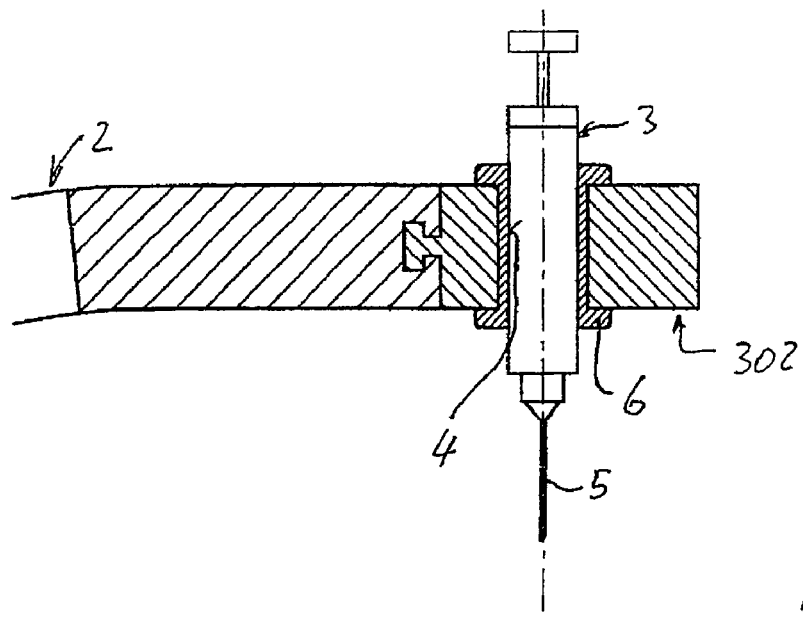
FIG. 5 shows an enlarged detail of the syringe supporting portion according to the embodiment of FIG. 4.
Figure 4:
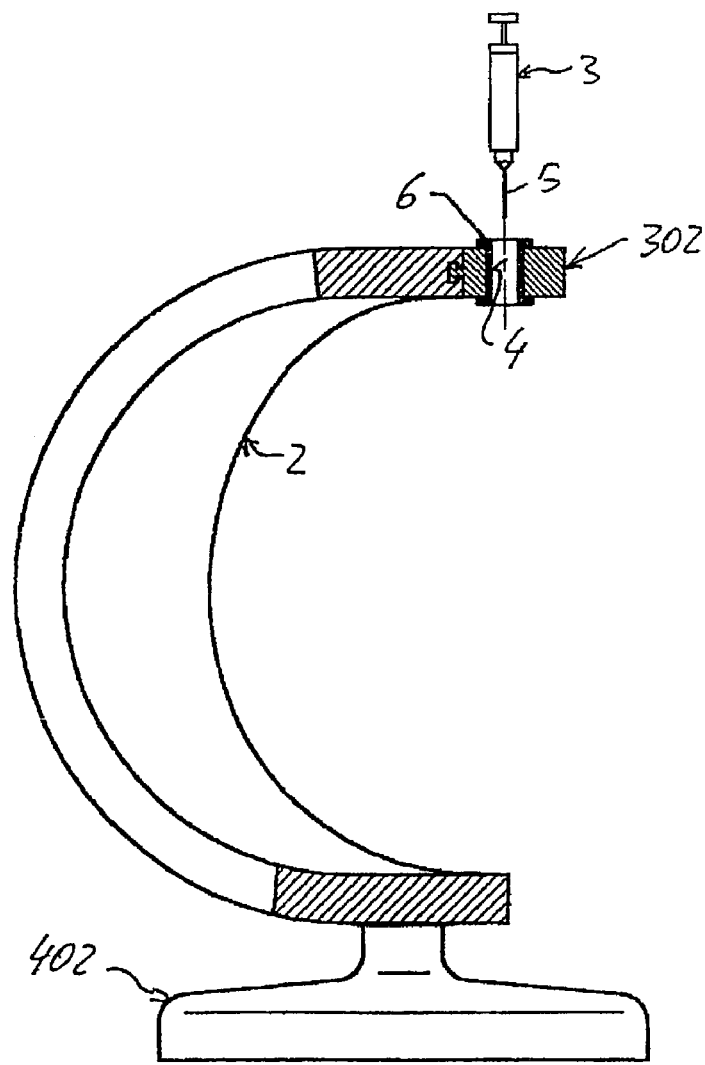
FIG. 4 is a sectional view of the area of the receiving coil as shown in FIG. 1 and having means for supporting an injection syringe.

In FIGS. 1 to 6 and 11, 12 variously shaped receiving coils 2 designed for the shoulder are shown. In FIGS. 1 and 4, the receiving coil 2 is arranged to have a C shape, i.e., open on one side for an easy introduction of the shoulder under examination, whereas in FIGS. 2, 3 to 6 and 11, 12 the coil 2 is made of a strap-shaped element having an essentially annular section, which requires the arm to be inserted therein to allow the coil 2 to reach the shoulder. In FIG. 2, the coil 2 is a substantially annular strap-shape element, which is additionally curved according to an axis perpendicular to the axis of the annular element. The coil 2 is applied on the shoulder in the same manner as the coil 2 of FIG. 1.

As widely described in the introduction, this embodiment of the invention provides that the coil 2 is provided with means for supporting a diagnostic and/or therapeutic tool and an ultrasound probe 22 of an ultrasound imaging apparatus combined with the MRI apparatus. Ultrasound imaging systems send ultrasound pulses in a region under examination and collect the reflected ultrasound pulse. The reflected pulses carry information about the reflectors which may be retrieved form the reflected pulses and transformed in image data that are printable on a monitor screen.

A wide variety of instrument types to be associated to the receiving coil 2 has been mentioned above. In the drawings, this instrument consists of an injection syringe 3, particularly for injecting contrast agents, which shall be only intended as a non-limiting example.

In the drawings many examples and embodiments of the supporting means having different features are shown with reference to the therapeutic tool, i.e., to the syringe. It is to be understood that for sake of simplicity the same means may be used in combination with the ultrasound probe also if this means has not been illustrated separately in combination with the probe, since this would consist in an unnecessary repetition of the features already disclosed in combination with the syringe.

In accordance with a particularly simple embodiment of the invention, the supporting means for the probe 22 and for the tool may consist of one or more through holes 4 formed in the enclosure of the coil 2 or in an external extension 302 thereof, and designed to accommodate each one respectively the syringe and the probe 22. These holes 4 may be formed in any position, particularly in an end portion, in the case of the C-shaped coil 2 and a median portion, in the case of the two annular coils 2. Obviously, the through holes 4 have such an internal size as to allow the syringe 3 and the probe 22 to be inserted in the corresponding hole 4 and to slide in the axial direction. Relating to the syringe the axial displacement allows the needle 5 to penetrate the body C under examination. Relating to the probe the axial displacement allows the probe to be brought in contact with the surface to be investigated also by ultrasound waves. In practice, in most cases, the holes will have a circular section with a slightly greater diameter than the diameter of the syringe body 3 and of the probe 22. Anyway, These holes 4 are an effective means for supporting and guiding the syringe 3 and the probe 22 and a good help for the operator. When the needle 5 of the syringe 3 is inside the imaging volume of the receiving coil 2, the aiming operations will be further facilitated by the possibility of simultaneously viewing the MRI images and the ecographic images of the tissues and of the needle 5.

Figure 6:
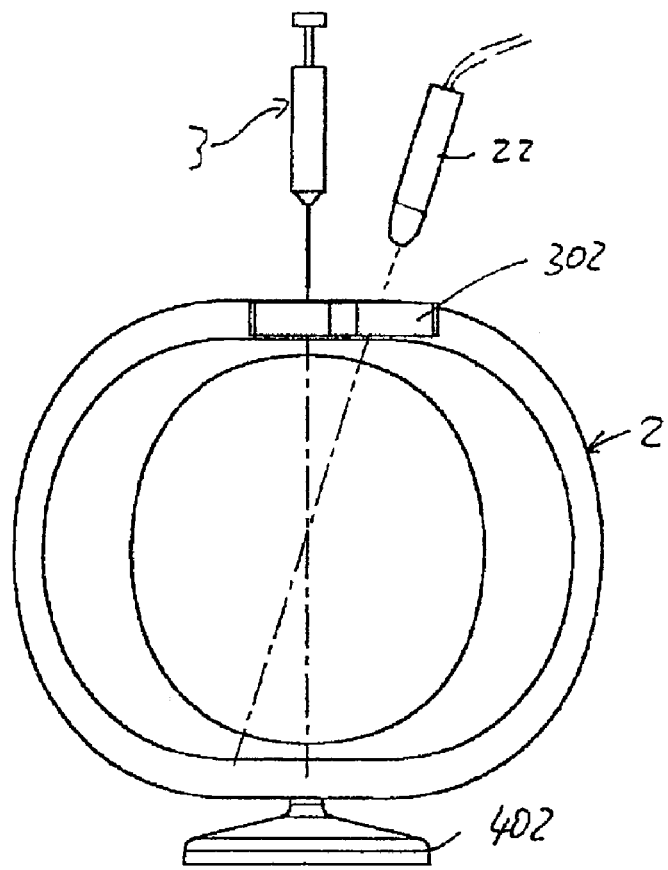
FIG. 6 shows an embodiment of a receiving coil having a double support for a needle or the like and an ultrasound probe for a combined MRI/US apparatus according to this invention.
Figure 7:
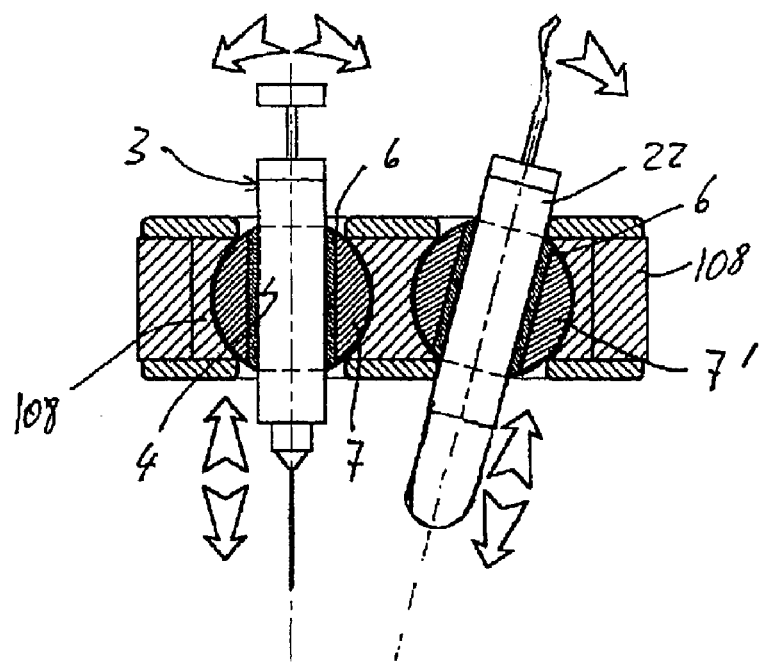
FIG. 7 is a sectional enlarged view of the needle supporting housings for the needle and the ultrasound probe according to the coil of FIG. 6.
Figure 8:
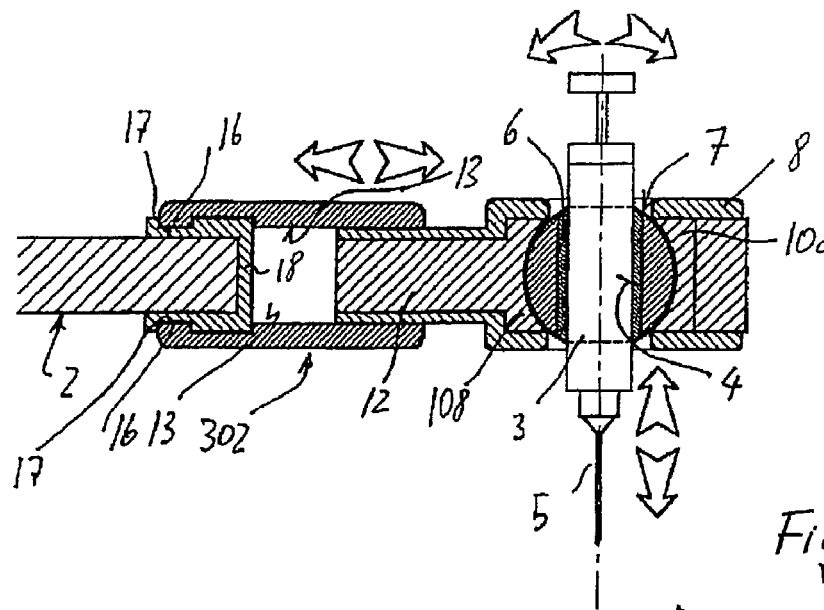
FIG. 8 is a sectional view of the syringe supporting portion, having a slide for translating the syringe and means for tilting the syringe.
Figure 9:
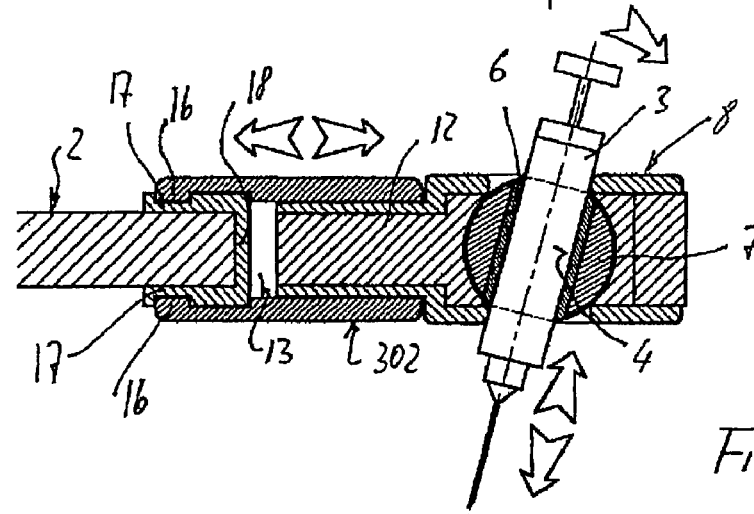
FIG. 9 is the same view as FIG. 8, the syringe being oriented with a different tilt angle with respect to FIG. 8.

According to an improvement, this through holes 4 may accommodate an interchangeable element for adaptation to the tool type and to the probe type which are to be used from time to time. The interchangeable elements may be a sleeve 6 wherein the syringe 3 and the probe 22 are introduced (FIGS. 6, 7). Obviously, the sleeves 6 have such an internal size and shape as to fit to the syringe 3 and to the probe 22. Furthermore the internal size and shape of the sleeves 6 is such as to allow the syringe 3 and/or the probe 22 to slide in their axial direction. The syringe 3 may slide freely inside the hole formed in the case or in the sleeve 6, or with the help, for instance, of a combination of slides and guides provided on the outer surface of the syringe body 3 and on the inner surface of the hole 4 respectively, or vice versa. Alternatively or in combination, this construction may be provided also for the probe 22.

In the embodiment as shown in FIG. 7, means are provided for tilting the syringe 3 and the probe 22 substantially in all directions turned toward the body under examination C and in a substantially vertical direction relative to the latter, for the purpose of improving the possibilities to aim the needle 5 and the probe 22. These means consist of a spherical element 7, 7' which acts as a swinging suspension element housed in a corresponding spherical seat 108 formed inside the thickness of the case, but preferably inside a support element 8 which is in turn attached to the case of the receiving coil 2. This spherical elements 7, 7' have a through hole 4 for the syringe 3 and for the probe 22 to be introduced and slide therein. Alternatively, any other swinging suspension element may be provided, for instance a gimbal which, as is known, is a joint with two perpendicular oscillation axes, allowing motion in all directions. According to an improvement, members may be provided to restrict the rotation of the elements 7, 7' inside the seat 108, e.g., small pads having such a construction as to generate a variable friction or one or more locking elements, or the like.

Figure 13:
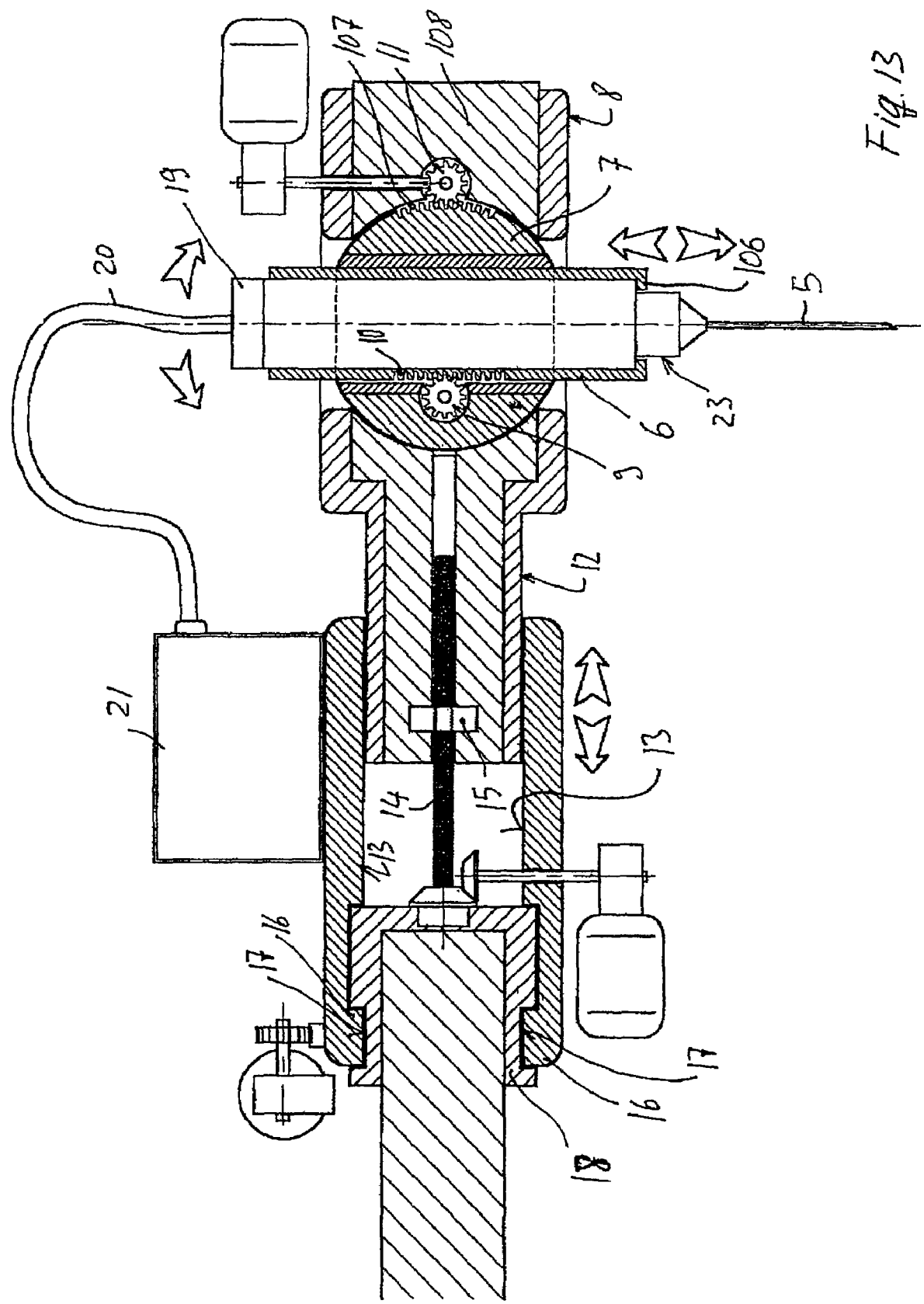

Motor driven means may be further provided allowing the syringe 3 and/or the probe 22 both to slide and be tilted (FIG. 13). This means are illustrated only with respect to the syringe 3 but may be provided alternatively or at the same time also for the probe 22, the construction of the above mentioned means being essentially identical also for the probe 22. In the first case of the said motor drive means, there is provided a combination of at least one motor driven pinion 9 and at least one corresponding rack-like linear set of teeth, arranged axially on the outer surface of the syringe 3 or possibly of the sleeve 6 in which the syringe 3 and/or the probe 22 is held. In the latter case, an advantageous arrangement consists in that the syringe 3 and/or the probe 22 are secured in the sleeve 6, e.g., by means which prevent it from projecting on the side toward the patient C, which may consist, for instance, of a suitable annular flange 106, which causes the diameter of the sleeve 6 to narrow at its end turned toward the patient C. Regarding the displacement of the spherical elements 7, 7' two rubber tracks may be provided on the surface thereof, each following half-meridians corresponding to perpendicular planes, whereon a small wheel splined on a driving motor or a gear 11 for engagement of a rack 107' shaped like a sector of a sphere 7, 7' rotates. Obviously, several other mechanical displacement arrangements, widely known per se, may be provided as an alternative thereto or in combination therewith.

Figure 11:
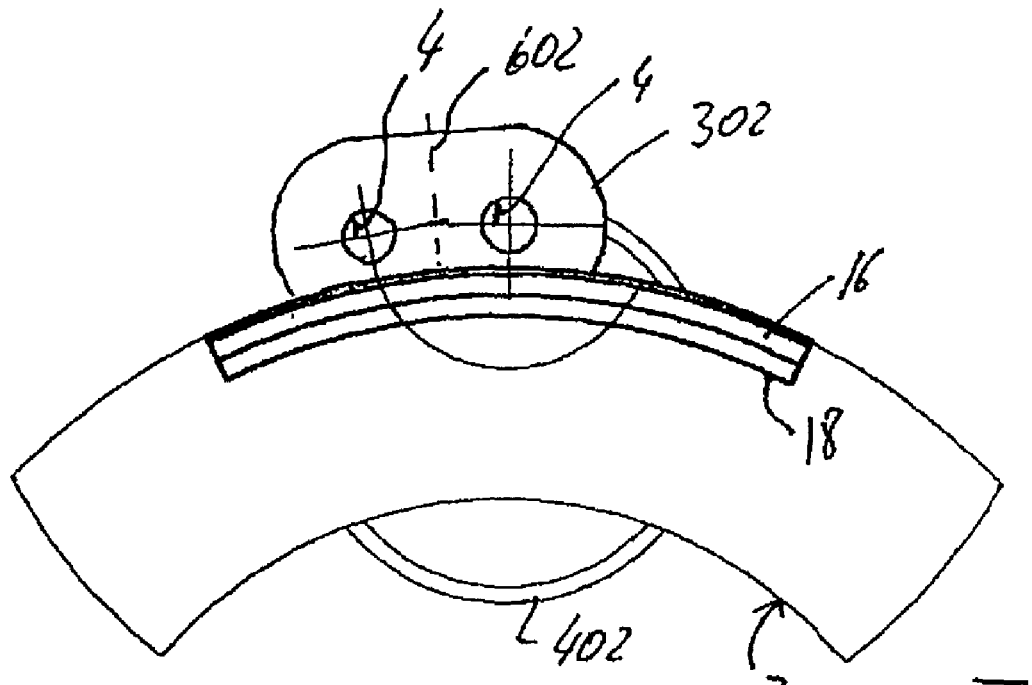
FIGS. 11 and 12 show top plan views of further embodiments of a receiving coil, with two types of translating guides for the support member for the ultrasound probe and for the diagnostic or therapeutic tool.
Figure 12:
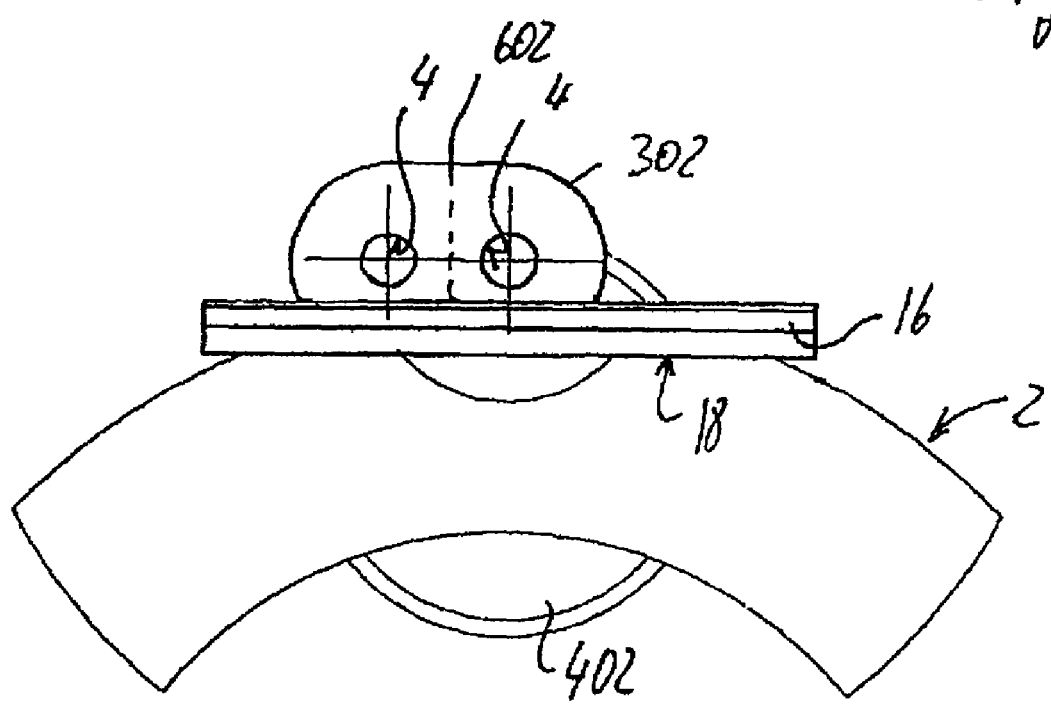

With reference to FIG. 13, the supporting element 8 is provided with means allowing displacement in two directions which are substantially perpendicular to each other and to the axis of the syringe 3 when the latter is not in the tilted condition. The displacement in the first direction, which is substantially radial with respect to the peripheral edge of the case is obtained by fitting the supporting element 8 at the external end of a carriage 12, particularly having a tubular shape, which is slidably engaged on guides 13. This movement may be motorized by providing a worm 14 which acts on an internally threaded bush 15, integral with the carriage 12. This bush 15 may be linked to a driving motor which causes the worm 14 to rotate and the carriage 12 to translate. The movement in the second direction which, as shown in FIGS. 11 and 12, may be a substantially coincident or parallel direction with respect to the peripheral edge of the case or in a direction corresponding to a line secant or tangent to said edge, is obtained by arranging the guides 13 to be in turn carried by an additional carriage 16 slidably engaged on an additional pair of guides 17 provided within a supporting element 18 attached to the peripheral edge. It shall be understood that all the above mechanical displacement arrangements are only provided by way of example, any other prior art arrangement being allowed.

All the guides illustrated herein, and particularly the translation guides 17 may be integrated in a hidden manner within the structure of the case of the receiving coil 2, as shown by the coils of FIGS. 2 and 3. Here, a slit allows the passage of a stirrup for connection with the carriage or the slide, sliding on the guide which follows the edge of the receiving coil.

Figure 10:
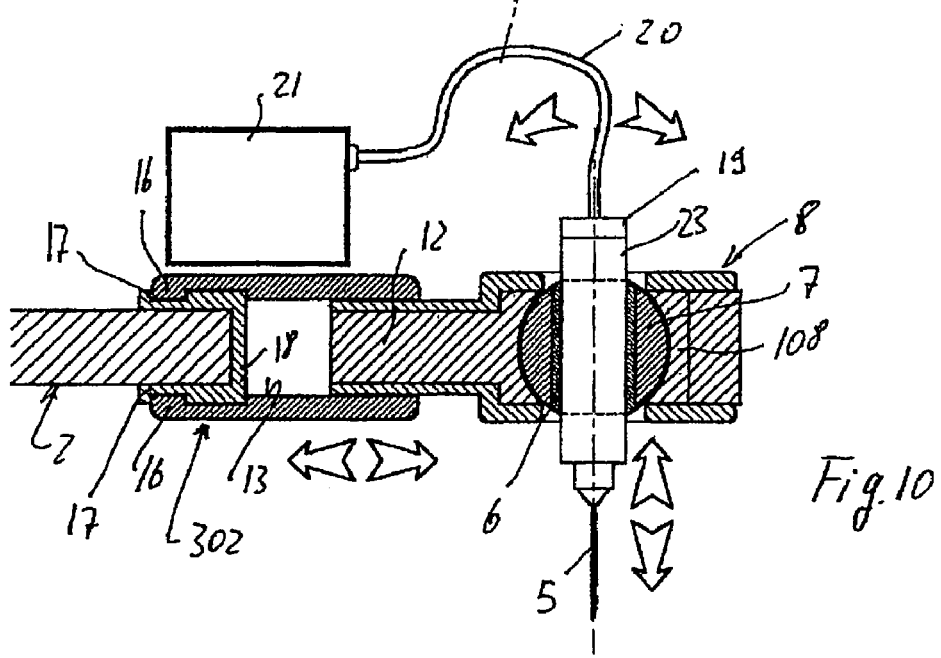
FIG. 10 is the same view as FIGS. 8 and 9, the coil having syringe tilting and translating means and dosing means for directly and automatically supplying the syringe.

In FIGS. 10 and 13, the diagnostic tool is an injection needle 23, particularly for injecting contrast agents. At the upper end, this has an element 19 for connection to a tube 20 linked to automatic dosing means 21 for supplying with a predetermined pressure the desired dose of contrast agent.

In FIG. 6, the guiding principle is shown as applied to a combined apparatus for simultaneous Magnetic Resonance and Ultrasound imaging. Each of the above diagnostic techniques has its own peculiar characteristics and is particularly suitable for imaging certain specific anatomic structures. The combined apparatuses tend to integrate both technologies, while trying to obtain as great an advantage as possible from each of them, for the purpose of obtaining as good a diagnostic image as possible, thanks to a good integration of the two images. Moreover, they generally allow to precisely detect the position of the ultrasound probe 22 with respect to the MRI volume, both to obtain the desired appropriate integration of the two images and to focus with a high accuracy the transmission of ultrasounds.

According to another feature of the invention the therapeutic tool may consist in a further ultrasound probe used as an ultrasound source for emitting ultrasound energy having surgical or therapeutic action, for instance for the destructive action they can exert on neoplastic tissues or the like.

In FIGS. 6 and 7, a syringe 3 for injecting contrast agents and an ultrasound probe 22, particularly for irradiating a shoulder with sound, are provided in an support element 8 which is appropriately oversized as compared with the one described above. Obviously the seat for the probe 22 shall be adapted to the conformation thereof. The ultrasound probe 22 itself is provided with means 7' which allow it to be tilted, whereas translation is performed by means shared by the two instruments and like those described above. Obviously, the probe may be arranged to be either of the manual operation and displacement type, or provided with its own separate means for displacement thereof along the part C under examination, distinct from those of the syringe 3. The signals from the ultrasound probe 22 and the receiving coil 2 may be advantageously processed with the well-known time sharing procedure which, as is known, provides that the electronic means for processing the received signals and for constructing a digital image formed by an array of pixels are at least partly the same for Magnetic Resonance signals and Ultrasound signals, particularly as regards equal imaging functions. These programs are executed alternately based on the type of corresponding received signal being processed from time to time.

It shall be noted that the means 8 for supporting the probe 22 may be such that the latter is at least partly located inside the MRI volume. This allows to integrate means for detecting the position of the probe 22 which may consist, for instance of one or more marking elements provided on the probe and recognizable by MRI.

It shall be also noted that the needle or any other similar diagnostic or therapeutic tool and the ultrasound probe may be supported in a simultaneous and substantially identical manner by one or more of the arrangements provided in this description as regards the needle only and in any combination or sub-combination thereof.

It is further important to consider that any other diagnostic or therapeutic tool may be provided in lieu of the ultrasound probe.

The ultrasound probe or any other tool and the needle or the like may be simultaneously supported in such a manner as to allow said two devices to be displaced with independent degrees of freedom or to only allow them to be displaced together with no possibility to change their relative position. To this end, the embodiment of FIGS. 6 and 7 only allows the needle and the probe to be tilted in different manners. An additional example may consist in providing a construction as shown in FIGS. 2, 3 and 11 and 12, wherein the same supporting member may be arranged to carry the needle or the like and the probe, the needle and the probe being only allowed to be displaced along the guide together and not independently from each other. Alternatively as shown by the dotted line indicated by the number 602 at least one additional movable probe supporting member is provided, which is displaced, for instance, along the same translation guide for the needle support or the like, but is wholly independent and unlinked from the needle supporting member or the like.

Obviously, the invention is not limited to the embodiments described and illustrated herein, but may be greatly varied, especially as regards construction, without departure from the guiding principle disclosed above and claimed below.

The invention claimed is:

1. An imaging apparatus, comprising:
   a magnetic resonance imaging apparatus having an imaging volume and at least one transmitting coil for exciting at least a part of a stationary body under examination within the imaging volume;
   at least one receiving coil within the imaging volume for receiving signals transmitted by the part of the stationary body under examination, said at least one receiving coil being housed within an enclosure;
   an electronic circuit for processing said received signals to create a diagnostic image;
   a device for supporting at least one diagnostic or therapeutic tool, said supporting device being attached to a peripheral portion of said enclosure so that the supporting device is disposed within the imaging volume;
   wherein said enclosure, and thereby said at least one receiving coil housed therewithin and said supporting device attached thereto, are portable so as to permit selective placement within the imaging volume relative to the part of the stationary body under examination;
   wherein the supporting device includes a first carriage which is slidable along a first guide having a first direction relative to a peripheral edge of the receiving coil enclosure, the first guide being carried on a second carriage which is slidable along a second guide having a second direction relative to the peripheral edge of the receiving coil enclosure; the second direction being different from the first direction; and
   wherein the supporting device has a through-hole which is oriented in a non parallel direction relative to the first and the second directions and which through-hole is designed to accommodate the at least one diagnostic or therapeutic tool with its axis parallel to the axis of the through-hole, the through-hole being provided in a tiltable swinging suspension formed by a spherical element housed in a spherical seat provided in the supporting device; the at least one diagnostic or therapeutic tool being axially slidable inside the through hole.

2. The apparatus as claimed in claim 1, further comprising:
   an ultrasound transmitting and receiving probe and an electronic circuit for driving the probe and for reconstructing an image from received ultrasound pulses and a support for the probe; the said support for the probe being formed by a further peripheral attachment of the enclosure of the receiving coil;
   the further peripheral attachment being a third carriage which is slidable along a third guide having a third direction relative to the peripheral edge of the receiving coil enclosure and further the third guide being carried on a fourth carriage which fourth carriage is slidable along the second guide, the third guide being different from the first guide for the carriage;
   the support for the probe having a through-hole which is oriented in a non parallel direction relative to the first and second directions and which through-hole is designed to accommodate the probe with it's axis parallel to the axis of the through-hole;
   the through-hole being provided in a tiltable swinging suspension formed by a spherical element housed in a spherical seat provided in the support for the probe;
   the probe being axially slidable inside the through hole;
   the support for the probe being slidable relative to the third and second guides separately from the supporting device for the tool.

3. The apparatus as claimed in claim 2, wherein the tool is adapted to be inserted into the part of the body.

4. The apparatus as claimed in claim 3, wherein the tool has an elongate shape.

5. The apparatus as claimed in claim 1, wherein said supporting device is provided in an internal position relative to the enclosure of the receiving coil.

6. The apparatus as claimed claim 1, wherein said supporting device has at least three degrees of freedom with respect to the enclosure of the receiving coil.

7. The apparatus as claimed in claim 1, wherein said supporting device allows the tool and/or the probe to be displaced independently in their axial direction.

8. The apparatus as claimed in claim 1, wherein said supporting device allows the tool and/or the probe to be displaced together in their axial direction.

9. The apparatus as claimed in claim 1, wherein said supporting device allows the tool to be tilted in at least two nonparallel, transverse planes, which contain an axis of the tool.

10. The apparatus as claimed in claim 1, wherein said supporting device allows the probe to be tilted in at least two nonparallel, transverse planes, which contain an axis of the probe.

11. The apparatus as claimed in claim 1, wherein said supporting device allows the tool and the probe to be tilted in every direction.

12. The apparatus as claimed in claim 1, wherein said supporting device allows the tool to be tilted in every direction.

13. The apparatus as claimed in claim 1, wherein said supporting device allows the probe to be tilted in every direction.

14. The apparatus as claimed in claim 1, wherein the through hole accommodates an interchangeable element allowing adaptation to a type of tool.

15. The apparatus as claimed in claim 1, wherein the tool has one or more slides for axial slidable engagement in corresponding guides provided on the inner surface of the through hole.

16. The apparatus as claimed in claim 1, wherein the probe has one or more slides for axial slidable engagement in corresponding guides provided on the inner surface of the through hole.

17. The apparatus as claimed in claim 1, wherein the tool may be displaced manually.

18. The apparatus as claimed in claim 1, wherein the tool may be displaced by a motor.

19. The apparatus as claimed in claim 18, wherein said motor comprises at least one combination of a motor driven pinion and of a corresponding rack.

20. The apparatus as claimed in claim 1, wherein diagnostic or therapeutic functions of the tool are operated manually.

21. The apparatus as claimed in claim 1, wherein diagnostic or therapeutic functions of the tool are operated automatically.

22. The apparatus as claimed in claim 1, wherein diagnostic or therapeutic functions of the probe are operated manually.

23. The apparatus as claimed in claim 1, wherein diagnostic or therapeutic functions of the probe are operated automatically.

24. The apparatus as claimed in claim 21, wherein automatic control means are provided for displacing or operating the tool.

25. The apparatus as claimed in claim 23, wherein automatic control means are provided for displacing or operating the probe.

26. The apparatus as claimed in claim 24, wherein said control means comprises one or more software programs loaded in a control unit which, after displaying and interpreting an acquired image, controls in a predetermined manner the tilt or displacement or operation of the tool.

27. The apparatus as claimed in claim 25, wherein said control means comprises one or more software programs loaded in a control unit which, after displaying and interpreting an acquired image, controls in a predetermined manner the tilt or displacement or operation of the probe.

28. The apparatus as claimed in claim 1, wherein said tool is a syringe for injecting contrast agents.

29. The apparatus as claimed in claim 1, wherein said tool is a needle for injecting contrast agents.

30. The apparatus as claimed in claim 28, further comprising means for automatically pushing the plunger of the syringe with an appropriate dose of a diagnostic or therapeutic substance.

31. The apparatus as claimed in claim 1, wherein said tool is a biopsy needle.

32. The apparatus as claimed in claim 1, wherein said tool is a microwave or RF antenna.

33. The apparatus as claimed in claim 1, wherein said tool is a cryotherapy probe.

34. The apparatus as claimed in claim 1, wherein said tool is an infrared probe.

35. The apparatus as claimed in claim 1, wherein said tool is an optical-fiber probe.

36. The apparatus as claimed in claim 1, wherein said tool is a surgical tool for cutterage or suction procedures.

37. The apparatus as claimed in claim 1, wherein said tool is an ultrasound source provided in combination with the probe.

38. The apparatus as claimed in claim 1, wherein the apparatus is a dedicated apparatus which has a size, and in which the receiving coil also has a size, for imaging only limited anatomic parts of a body under examination.

39. The apparatus as claimed in claim 38, wherein the anatomic parts are shoulders.

40. The apparatus as claimed in claim 39, wherein the apparatus is provided with a shoulder imaging coil of a closed type having an essentially annular shape.

41. The apparatus as claimed in claim 39, wherein the apparatus is provided with a shoulder imaging coil of an open type having a C shape.

42. The apparatus as claimed in claim 1, wherein the apparatus is a combined apparatus used for Magnetic Resonance imaging and ultrasound imaging, operating in a time-sharing mode.

43. The apparatus as claimed in claim 42, wherein the probe includes means for detecting a position of the probe by MRI, so that positions of the individual ultrasound scan sections may be defined relative to MRI images and that the desired relations between the two image types may be established.

44. The apparatus as claimed in claim 43, wherein the support for the probe or the probe itself has analog or digital, mechanical, electromechanical, electronic or optoelectronic means for detecting the position of the probe relative to the part of the body under examination or to the Magnetic Resonance imaging volume.

45. An imaging apparatus, comprising:
a magnetic resonance imaging apparatus with at least one transmitting coil for exciting at least a part of a body under examination;
at least one coil for receiving signals transmitted by the part of the body under examination;
an electronic circuit for processing said received signals to create a diagnostic image;
a device for supporting at least one diagnostic or therapeutic tool;
the receiving coil being housed within an enclosure;

the supporting device being an external extension of a peripheral portion of the receiving coil enclosure and including a first carriage which is slidable along a first guide having a first direction relative to a peripheral edge of the receiving coil enclosure and further the first guide being carried on a second carriage which second carriage is slidable along a second guide having a second direction relative to the peripheral edge of the receiving coil enclosure; the second direction being different from the first direction;

the supporting device the tool having a through-hole which is oriented in a non parallel direction relative to the first and the second directions and which through-hole is designed to accommodate the tool with its axis parallel to the axis of the through-hole, the through-hole being provided in a tiltable swinging suspension formed by a spherical element housed in a spherical seat provided in the external extension; the tool being axially slidable inside the through hole;

further comprising an ultrasound transmitting and receiving probe and an electronic circuit for driving the probe and for reconstructing an image from received ultrasound pulses and a support for the probe; the support for the probe being formed by a further external extension of the enclosure of the receiving coil;

the further external extension being a third carriage which is slidable along a third guide having a third direction relative to the peripheral edge of the receiving coil enclosure and further the third guide being carried on a fourth carriage which fourth carriage is slidable along the second guide, the third guide being different from the first guide for the carriage forming the external extension supporting the tool;

the support for the probe having a through-hole which is oriented in a non parallel direction relative to the first and second directions and which through-hole is designed to accommodate the probe with it's axis parallel to the axis of the through-hole, the through-hole being provided in a tiltable swinging suspension formed by a spherical element housed in a spherical seat provided in the further external extension;

the probe being axially slidable inside the through hole;

the support for the probe being slidable relative to the third and second guides separately from the supporting device for the tool;

in which means are provided for connecting together the carriages supporting the first guide associated to the tool supporting device and the first guide for the support of the probe, so that the said carriages slides together along the common second guide.

46. An imaging apparatus, comprising:

a magnetic resonance imaging apparatus having an imaging volume and at least one transmitting coil for exciting at least a part of a body under examination within the imaging volume;

at least one portable coil adapted for selective placement within the imaging volume for receiving signals transmitted by the part of the body under examination;

an electronic circuit for processing said received signals to create a diagnostic image;

a device for supporting at least one diagnostic or therapeutic tool;

an ultrasound imaging apparatus having an ultrasound transmitting and receiving probe and an electronic circuit for driving the probe and for reconstructing an image from the received ultrasound pulses; and a support for the probe;

wherein the device for supporting the tool and the support for the probe are both supported by the at least one portable receiving coil so as to permit selective placement within the imaging volume relative to the part of the body under examination.

47. The apparatus as claimed in claim 1, wherein said enclosure includes a pedestal.

* * * * *